United States Patent [19]
Hutchinson

[11] 3,940,342
[45] Feb. 24, 1976

[54] AZEOTROPE OF 1,2-DICHLORO-1,1,2-TRIFLUOROETHANE AND TRICHLOROFLUOROMETHANE

[75] Inventor: William M. Hutchinson, Bartlesville, Okla.

[73] Assignee: Phillips Petroleum Company, Bartlesville, Okla.

[22] Filed: Sept. 13, 1973

[21] Appl. No.: 396,814

[52] U.S. Cl. .................. 252/171; 252/67; 252/162; 252/305; 252/364; 252/DIG. 9
[51] Int. Cl.² ...................... C11D 7/50; C23G 5/02
[58] Field of Search ...... 252/DIG. 9, 170, 171, 172, 252/364, 66–68; 264/DIG. 5; 260/652.5 R, 652.5 P

[56] References Cited
UNITED STATES PATENTS

| | | | |
|---|---|---|---|
| 2,999,816 | 9/1961 | Bennett et al. | 252/171 |
| 3,332,881 | 7/1967 | Burt et al. | 252/162 |
| 3,349,009 | 10/1967 | Ruehlen | 203/67 |
| 3,391,204 | 7/1968 | Young | 260/653 |

*Primary Examiner*—Samuel Feinberg
*Assistant Examiner*—Ralph Palo

[57] ABSTRACT

Constant boiling binary admixtures are formed by 1,2-dichloro-1,1,2-trifluoroethane with trichlorofluoromethane, with diethyl ether, and with dichloromethane. A constant boiling ternary admixture is formed by 1,2-dichloro-1,1,2-trifluoroethane, diethyl ether, and 1,2-dibromo-1,1,2,2-tetrafluoroethane.

5 Claims, No Drawings

AZEOTROPE OF 1,2-DICHLORO-1,1,2-TRIFLUOROETHANE AND TRICHLOROFLUOROMETHANE

FIELD OF THE INVENTION

The invention relates to novel compositions of matter incorporating 1,2-dichloro-1,1,2-trifluoroethane.

BRIEF SUMMARY OF THE INVENTION

I have discovered that 1,2-dichloro-1,1,2-trifluoroethane forms a binary constant boiling admixture with trichlorofluoromethane; a binary constant boiling admixture with diethyl ether; a binary constant boiling admixture with dichloromethane; and a ternary constant boiling admixture with 1,2-dibromo-1,1,2,2-tetrafluoroethane and diethyl ether. These constant boiling admixtures can be termed azeotropes.

DETAILED DESCRIPTION OF THE INVENTION

The binary composition 1,2-dichloro-1,1,2-trifluoroethane with trichlorofluoromethane is characterized by a boiling point of about 23°–24° C at a pressure of about 742–744 mm/Hg. The weight relationship is about 28–29 weight percent 1,2-dichloro-1,1,2-trifluoroethane and correspondingly about 72–71 weight percent trichlorofluoromethane. This constant boiling admixture exhibits the characteristics typical of an azeotrope.

The binary constant boiling admixture of 1,2-dichloro-1,1,2-trifluoroethane with diethyl ether is characterized by a boiling point of about 38°–39° C at a pressure of about 735–743 mm/Hg. This binary constant boiling admixture surprisingly is characterized by a relatively broad range of relative composition, yet with unusual constancy of boiling point. The weight relationship is in the range of about 58 to 60 weight percent 1,2-dichloro-1,1,2-trifluoroethane and correspondingly about 42 to 40 weight percent diethyl ether. The azeotropic compositions contain about 59.8 weight percent 1,2-dichloro-1,1,2-trifluoroethane and 40 weight percent diethyl ether at about 735–736 mm mercury, or about 58.9:41.1 at about 742–743 mm mercury, and exhibit the characteristics typical of azeotropes.

The binary constant boiling admixture 1,2-dichloro-1,1,2-trifluoroethane with dichloromethane is characterized by a boiling point of about 29.4° C at 743 mm mercury pressure. The weight relationship is about 88.6 weight percent 1,2-dichloro-1,1,2-trifluoroethane and correspondingly 11.4 weight percent dichloromethane. This constant boiling admixture exhibits the characteristics typical of an azeotrope.

The ternary constant boiling admixture of 1,2-dichloro-1,1,2-trifluoroethane with 1,2-dibromo-1,1,2,2-tetrafluoroethane and diethyl ether is characterized by a boiling point of about 38°–39° C at a pressure of about 740–741 mm/Hg. The weight relationship is about 53.3:11.2:35.5 characterized at a boiling point of about 38.8° C at about 740.8 mm/Hg. The composition exhibits the characteristics typical of an azeotrope.

Constant boiling admixtures are liquid mixtures of two or more substances which mixtures behave like a single substance in that the vapor produced by partial evaporation or distillation has the same composition as does the liquid, i.e., the admixtures distill without change in composition. Constant boiling compositions characterized as azeotropes exhibit either a maximum or minimum boiling point as compared with that of nonazeotropic mixtures of the same substances. It is not possible to predict what two or more substances will combine to form azeotropes.

At differing pressures, the composition of a given azeotrope will vary, at least slightly, and changes in distillation pressures also change, at least slightly, the distillation temperatures. Thus an azeotrope of A and B represents a unique type of relationship but with a variable composition.

It is possible to fingerprint, in effect, a constant boiling admixture which may appear under varying guises depending on the conditions chosen by any of several criteria: the composition can be defined as an azeotrope of A and B, since the very term "azeotrope" is at once both definitive and limitative, requiring that A and B indeed form this unique composition of matter which is a constant boiling admixture. Or, the composition can be defined as a particular weight percent relationship or mole percent relationship of A:B, while recognizing that such specific values point out only one particular such relationship and that in actuality a series of such relationships represented by A:B actually exist for a given azeotrope, varied by influence of distillative conditions chosen, the temperature and pressure relationship. Or, recognizing that the azeotrope A:B does represent just such a series of relationships, the azeotropic series represented by A:B can be characterized by defining the composition as an azeotrope characterized by a boiling point at a given pressure, thus giving identifying characteristics without unduly limiting the scope of the invention by a specific numerical composition which is limited by and is only as accurate as the analytical equipment available. The same considerations are applicable to both binary azeotropes A:B and to ternary azeotropes A:B:C.

EXAMPLES

The following experimentally measured data are presented in order to assist in disclosing and describing my invention, and, therefore, are not intended to be limitative of the reasonable scope thereof.

The constant boiling admixtures of my invention were prepared by distilling binary or ternary admixtures until the overhead temperature reached a constant value, and the composition of distillate remained unchanged as verified by GLC (Gas-Liquid Chromatography) analysis, thereby establishing the existence of the minimum or maximum boiling azeotrope in each case.

The still employed was an Ace Glass Company Catalog No. 9219, concentric tube column about 13 inches long, about 10 mm internal diameter, silvered vacuum jacket, rated 40 plates at 80 cc/hr boil-up rate, equipped with a vacuum jacketed head with magnetic take-off fitted with a copper-constantan thermocouple and Thermoelectric Minimite potentiometer giving temperature readings within 0.2° C accuracy, a graduated receiver, and a 25 cc conical kettle heated by a mantle and wrapped in glass wool. The condenser was a cold-finger type cooled by trichlorofluoromethane and dry ice. The receiver was cooled to prevent reboiling and consequent loss. Distillations were at atmospheric pressure, and the atmospheric pressure was measured frequently with a calibrated aneroid barometer graduated in mm/Hg. Product of the distillation was analyzed with an Aerograph 1520 gas chromatograph having a disc integrator on its recorder.

EXAMPLE I

A mixture of about 48 weight percent 1,2-dichloro-1,1,2-trifluoroethane and 52 weight percent trichlorofluoromethane was charged to the kettle, heated to its atmospheric boiling point, and distilled, employing a reflux ratio of 40:1. A minimum boiling overhead binary azeotropic mixture was obtained with a composition of about 28.4 weight percent 1,2-dichloro-1,1,2-trifluoroethane and correspondingly about 71.6 weight percent trichlorofluoromethane. This constant boiling admixture, exhibiting the characteristics of an azeotrope, was obtained at a boiling point of about 23.5° C at about 742.9 mm/Hg pressure. The azeotrope was nonflammable. Distillation data are shown in Table I below:

Table I

| Overhead Distillation Temperature °C | Overhead Fraction No. | Cumulative Overhead Fractions %(a) | Overhead Composition, Percent Weight | |
|---|---|---|---|---|
| | | | F-123A(b) | F-11(c) |
| 23.6/23.5 | 1 | 3 | 28 | 72 |
| 23.5/23.6 | 2 | 15 | 28.4 | 71.6 |
| 23.6/23.9 | 3 | 38 | 28 | 72 |

(a) Volume % of charge to distillation kettle.
(b) 1,2-Dichloro-1,1,2-trifluoroethane.
(c) Trichlorofluoromethane.

Compositions in the range of about 28–29 weight percent 1,2-dichloro-1,1,2-trifluoroethane and correspondingly about 72–71 weight percent trifluoroethane are considered to be within the scope of my invention, boiling at about 23°–24° C, at about 742–744 mm/Hg pressure. The azeotropic composition itself, considering the analytical equipment, appears to be more nearly 28.4 weight percent 1,2-dichloro-1,1,2-trifluoroethane and correspondingly about 71.6 weight percent trichlorofluoromethane, azeotropic boiling point 23.5° C measured at 742.9 mm/Hg. The azeotropic was nonflammable, and was found to be particularly useful as a rosin (solder flux) solvent.

EXAMPLE II

A mixture of 38.4 weight percent 1,2-dichloro-1,1,2-trifluoroethane and 61.6 weight percent diethyl ether was charged to the kettle, heated to its boiling point at atmospheric pressure, and distilled while employing a reflux ratio of 40:1. A constant boiling admixture was observed, and the data indicate a maximum boiling binary azeotrope was obtained at about 38.6° C at a measured pressure of about 742.4 mm/Hg pressure. Analysis indicated a composition of about 58.9 weight percent 1,2-dichloro-1,1,2-trifluoroethane and correspondingly about 41.1 weight percent diethyl ether. Distillation data are shown in the following Table II:

Table II

| Fraction | Head Temperature °C | Pressure mm/Hg | Cumulative Overhead Fractions(a) | Overhead Composition, Weight Percent | |
|---|---|---|---|---|---|
| | | | | diethyl ether | F-123a |
| 1 | 33.8/33.8 | 741.7 | 2 | 100 | 0.0 |
| 2 | 33.8/34.0 | 741.7 | 15 | 100 | 0.0 |
| 3 | 34.0/34.2 | 741.6 | 21 | 99.5 | 0.5 |
| 4 | 34.2/34.3 | 741.2 | 27 | 99 | 1 |
| 5 | 34.3/34.6 | 741.8 | 30 | 87 | 13 |
| 6 | 34.6/35.0 | 741.7 | 32 | 80 | 20 |
| 7 | 35.0/37.2 | 741.7 | 40 | 65 | 35 |
| 8 | 37.2/37.6 | 741.7 | 42 | 55 | 45 |
| 9 | 37.6/38.1 | 742.0 | 45 | 50 | 50 |
| 10 | 38.1/38.3 | 741.9 | 50 | 44 | 56 |
| 11 | 38.3/38.4 | 741.8 | 53 | 42 | 58 |
| 12 | 38.4/38.4 | 741.4 | 56 | 41 | 59 |
| 13 | 38.4/38.5 | 741.6 | 62 | 41 | 59 |
| 14 | 38.5/38.5 | 741.9 | 65 | 41 | 59 |
| 15 | 38.5/38.5 | 741.9 | 70 | 41 | 59 |
| 16 | 38.5/38.6 | 742.1 | 75 | 41.1 | 58.9 |
| 17 | 38.6/38.6 | 742.5 | 80 | 41.4 | 58.6 |
| 18 | 38.6/38.6 | 742.3 | 87 | 40.8 | 59.2 |

(a) Volume percent of charge to kettle.

In another run, a mixture of 60 weight percent 1,2-dichloro-1,1,2-trifluoroethane and 40 weight percent diethyl ether was charged to the kettle, heated to its boiling point at atmospheric pressure, and distilled while employing a reflux ratio of 40:1. A constant boiling admixture was observed, and the data indicate a maximum boiling binary azeotrope was obtained at about 38.3° C at a measured pressure of about 735.5 mm/Hg pressure. Analysis indicated a composition of about 59.8 weight percent 1,2-dichloro-1,1,2-trifluoroethane and correspondingly about 40.2 weight percent diethyl ether. Distillation data are shown in the following Table III:

Table III

| Fraction | Head Temperature °C | Pressure mm/Hg | Cumulative Overhead Fractions(a) | Overhead Composition, Weight Percent | |
|---|---|---|---|---|---|
| | | | | diethyl ether | F-123a |
| 1 | 38.0/38.0 | 735.1 | 2 | 41.5 | 58.5 |
| 2 | 38.0/38.2 | 735.1 | 8 | 41.6 | 58.4 |
| 3 | 38.2/38.3 | 735.2 | 13 | 40.7 | 59.3 |
| 4 | 38.3/38.3 | 735.4 | 17 | 40.4 | 59.6 |
| 5 | 38.3/38.3 | 735.6 | 21 | 39.9 | 60.1 |

(a) Volume percent of charge to kettle.

This azeotrope was flammable. This azeotrope was found to be particularly useful solvent for fats. Fats float on this azeotrope. It is suggested that hides could be floated on this solvent while being defatted before tanning.

EXAMPLE III

A mixture of 34.7 weight percent dichloromethane ($CH_2Cl_2$) and 65.3 weight percent 1,2-dichloro-1,1,2-trifluoroethane was charged to the kettle and heated under atmospheric pressure to the boiling point and distilled at a reflux ratio of 20:1. Distillation data are shown below:

Table IV

| Fraction | Head Temperature | Pressure | Cumulative Overhead Fraction(a) | Overhead Composition Weight Percent | |
|---|---|---|---|---|---|
| | | | | F-123a | $CH_2Cl_2$ |
| 1 | 30.4/30.1 | 744.0 | 7 | — | — |
| 2 | 30.1/29.4 | 743.8 | 14 | — | — |
| 3 | 29.4/29.4 | 743.6 | 20 | — | — |
| 4 | 29.4/29.4 | 743.6 | 35 | 88.4 | 11.6 |
| 5 | 29.4/29.4 | 743.0 | 50 | 88.6 | 11.4 |

(a) Volume percent charge to kettle.

An azeotrope was obtained as the constant-boiling constant-composition mixture of about 88.6 weight percent 1,2-dichloro-1,1,2-trifluoroethane and 11.4 weight percent dichloromethane at about 743 mm Hg pressure. The azeotrope boiling point was about 29.4° C.

EXAMPLE IV

A mixture of 50 weight percent 1,2-dichloro-1,1,2-trifluoroethane and 17 weight percent 1,2-dibromo-1,1,2,2-tetrafluoroethane and 33 weight percent diethyl ether was charged to the kettle, heated to the boiling point at atmospheric pressure, and distilled employing a reflux ratio of 40:1. One ternary azeotropic admixture was determined. Distillation data are as follows:

Table V

| Fraction No. | Head Temperature °C | Pressure mm/Hg | Cumulative Overhead Fraction(a) | Overhead Composition Weight Percent | | |
|---|---|---|---|---|---|---|
| | | | | F-123a | F-114B2(c) | DEE |
| 1 | 38.2/38.1 | 735.6 | 2 | 62.4 | 5.7 | 31.9 |
| 2 | 38.1/38.3 | 735.1 | 8 | 63.3 | 7.0 | 29.7 |
| 3 | 38.3/38.4 | 735.6 | 12 | 60.2 | 7.3 | 32.5 |
| 4 | 38.4/38.6 | 736.1 | 21 | 57.1 | 8.1 | 34.8 |
| 5 | 38.6/38.7 | 736.4 | 26 | 56 | 9 | 35 |
| 6 | 38.8/38.8 | 740.8 | 27 | 53.0 | 11.8 | 35.2 |
| 7 | 38.8/38.8 | 740.8 | 31 | 53.5 | 10.6 | 35.9 |

(a)Volume percent of charge to kettle.
(c)1,2-dibromo-1,1,2,2-tetrafluoroethane.

According to the data shown, a maximum boiling ternary azeotrope was obtained exhibiting a boiling point of about 38.8° C measured at about 740.8 mm/Hg pressure. This constant boiling admixture on analysis was found to contain about 53.3 weight percent 1,2-dichloro-1,1,2-trifluoroethane, 11.2 weight percent 1,2-dibromo-1,1,2,2-tetrachloroethane, and 35.5 weight percent diethyl ether. This azeotrope was nonflammable.

The compositions of my invention have applications as solvents for greases, oils, and waxes; as aerosol propellants; in cleaning or dissolving rosin solder flux; in cleaning electric motors, compressors, photographic films, oxygen storage tanks, lithographic plates, typewriters, precision instruments, gauges, and sound tape; for cleaning of cloth, clothing wool, hides, and the like.

I claim:

1. The substantially constant boiling admixture of (A) 1, 2 -dichloro- 1, 1, 2-trifluoroethane and (B) trichlorofluoromethane which at substantially atmospheric pressure is characterized as about 28–29 weight percent (A) and about 72–71 weight percent (B).

2. A substantially constant boiling admixture according to claim 1 further characterized as an azeotrope.

3. The azeotropic admixture according to claim 2 characterized by a boiling point of about 23.5° C at about 742.9 mm/Hg.

4. The azeotropic composition according to claim 2 wherein said (A) represents about 28.4 weight percent, and said (B) about 71.6 weight percent.

5. A substantially constant boiling admixture according to claim 1 characterized by a boiling temperature of about 23°–24° C at a pressure of about 742–744 mm/Hg.

* * * * *